United States Patent
Hirata

(10) Patent No.: US 9,442,586 B2
(45) Date of Patent: Sep. 13, 2016

(54) SIGNAL PROCESSING DEVICE, TOUCH PANEL UNIT, INFORMATION PROCESSOR, AND SIGNAL PROCESSING METHOD

(71) Applicant: Sony Computer Entertainment Inc., Tokyo (JP)

(72) Inventor: Shinichi Hirata, Kanagawa (JP)

(73) Assignees: Sony Corporation, Tokyo (JP); Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 13/921,541

(22) Filed: Jun. 19, 2013

(65) Prior Publication Data

US 2014/0375571 A1 Dec. 25, 2014

Related U.S. Application Data

(63) Continuation of application No. PCT/JP2011/007087, filed on Dec. 19, 2011.

(30) Foreign Application Priority Data

Dec. 22, 2010 (JP) .................................. 2010-286240

(51) Int. Cl.
  *G06F 3/041* (2006.01)
  *A61B 5/00* (2006.01)
  *A61B 5/0245* (2006.01)
  *A61B 5/04* (2006.01)
  (Continued)

(52) U.S. Cl.
  CPC ............. *G06F 3/041* (2013.01); *A61B 5/0245* (2013.01); *A61B 5/04014* (2013.01); *A61B 5/7257* (2013.01); *A61B 5/7282* (2013.01); *G06F 3/044* (2013.01); *G06F 3/0416* (2013.01); *G06F 3/0488* (2013.01); *A61B 5/02438* (2013.01); *A63F 2300/1075* (2013.01); *A63F 2300/204* (2013.01); *A63F 2300/6045* (2013.01); *G06F 2203/04104* (2013.01)

(58) Field of Classification Search
  None
  See application file for complete search history.

(56) References Cited

U.S. PATENT DOCUMENTS 7,254,775 B2 8/2007 Cordeiro
7,548,891 B2 6/2009 Ono
(Continued)

FOREIGN PATENT DOCUMENTS

CN 1692341 A 11/2005
CN 1745696 A 3/2006
(Continued)

OTHER PUBLICATIONS

Office Action for corresponding Chinese Patent Application No. 201180061717.1, dated Aug. 20, 2014.
(Continued)

*Primary Examiner* — Kenneth B Lee, Jr.
(74) *Attorney, Agent, or Firm* — Matthew B. Dernier, Esq.

(57) ABSTRACT

A sampling unit acquires a sample data series of a signal indicating a touch state quantity detected in a touch panel. A discrete Fourier transformation unit transforms the sample data series into the frequency domain. The frequency spectral analysis unit determines a frequency spectral distribution in accordance with the sample data transformed into the frequency domain. A peak detection unit detects a peak in a frequency band of a pulse in the frequency spectral distribution and finds the frequency of the detected peak so as to determine the pulse.

12 Claims, 8 Drawing Sheets

(51) Int. Cl.
*G06F 3/0488* (2013.01)
*G06F 3/044* (2006.01)
*A61B 5/024* (2006.01)

(56) References Cited

U.S. PATENT DOCUMENTS

| | | | |
|---|---|---|---|
| 2003/0036685 A1 | 2/2003 | Goodman | |
| 2003/0063073 A1 | 4/2003 | Cordeiro | |
| 2004/0267140 A1* | 12/2004 | Ito et al. | 600/500 |
| 2005/0149467 A1 | 7/2005 | Ono | |
| 2006/0220788 A1 | 10/2006 | Dietz | |
| 2007/0291012 A1* | 12/2007 | Chang | 345/173 |
| 2009/0289911 A1 | 11/2009 | Nagai | |
| 2010/0249494 A1 | 9/2010 | Furuta | |
| 2011/0009193 A1 | 1/2011 | Bond | |
| 2013/0231186 A1 | 9/2013 | Furuta | |

FOREIGN PATENT DOCUMENTS

| | | |
|---|---|---|
| JP | 2003331268 A | 11/2003 |
| JP | 2005505065 A | 2/2005 |
| JP | 2005095581 A | 4/2005 |
| JP | 2006304264 A | 11/2006 |
| JP | 2009282634 A | 12/2009 |
| JP | 2010026064 A | 2/2010 |
| JP | 2010035560 A | 2/2010 |
| JP | 2010231399 A | 10/2010 |

OTHER PUBLICATIONS

International Search Report for the corresponding PCT Application No. PCT/JP2011/007087, dated Mar. 19, 2012.
International Preliminary Examination Report on Patentability with Written Opinion for the corresponding PCT Application No. PCT/JP2011/007087, dated Jul. 2, 2013.
Office Action for corresponding Japanese Patent Application No. 2010-286240, dated Dec. 24, 2014.

* cited by examiner

SIGNAL PROCESSING DEVICE, TOUCH PANEL UNIT, INFORMATION PROCESSOR, AND SIGNAL PROCESSING METHOD

BACKGROUND OF THE INVENTION

1. Field of the Invention

The present invention relates to an apparatus and a method for processing a signal detected in a touch panel.

2. Description of the Related Art

Interface devices including touch panels and touch pads, to which inputs can be made when a person directly touches the display screen of the device using a finger, are widely used in personal computers, various mobile devices, cellular phones, and the likes. Also, there have been recently developed devices that can acquire attribute information on a touch point besides the coordinates thereof, such as the strength (pressure) of the touch and the direction of the finger.

Patent document 1 discloses a portable image display apparatus provided with display screens on both the front and rear surfaces.

[patent document 1] Japanese Patent Application Laid-open No. 2010-26064.

Users can use the touch panel or the touch pad to enter a variety of information through user operation on the screen. However, devices capable of acknowledging input of biological information of human beings have not been available. Measurement of the pulsation as biological information requires equipment exclusively used for that purpose such as a pulse monitor provided with a pulse sensor for measuring the pulse by using the property of hemoglobin in the bloodstream to absorb infrared light and so requires high cost.

SUMMARY OF THE INVENTION

The present invention addresses the problem and a purpose thereof is to provide a technology capable of acquiring information related to the pulse by using a touch panel.

In order to address the problem, a signal processing device according to one embodiment of the present invention comprises: a sampling unit configured to acquire a sample data series of a signal indicating a touch state quantity detected in a touch panel; an analysis unit configured to determine a frequency spectral distribution by transforming the sample data series into a frequency domain; and a peak detection unit configured to detect a peak in a frequency band of a pulse in the frequency spectral distribution, and to find a frequency of the detected peak so as to determine the pulse.

Another embodiment of the present invention relates to a touch panel. The touch panel unit comprises: a touch panel; and a touch panel controller configured to detect a position of a touch point on the touch panel and a touch state quantity and to output the position and the quantity as a signal. The touch panel controller includes: a sampling unit configured to acquire a sample data series of a signal indicating the touch state quantity; an analysis unit configured to determine a frequency spectral distribution by transforming the sample data series into a frequency domain; and a peak detection unit configured to detect a peak in a frequency band of a pulse in a frequency spectral distribution, and to find a frequency of the detected peak so as to determine the pulse.

Still another embodiment of the present invention relates to an information processing device. The device comprises: a touch panel unit including a touch panel and a touch panel controller configured to detect a position of a touch point on the touch panel and a touch state quantity and to output the position and the quantity as a signal; a signal processing unit configured to subject an output signal from the touch panel controller to signal processing; a main processor configured to run an application; and a display controller configured to control data that should be displayed on a display device provided in the touch panel. The signal processing unit includes: a sampling unit configured to acquire a sample data series of a signal indicating a touch state quantity detected in a touch panel; an analysis unit configured to determine a frequency spectral distribution by transforming the sample data series into a frequency domain; and a peak detection unit configured to detect a peak in a frequency band of a pulse in the frequency spectral distribution, and to find a frequency of the detected peak so as to determine the pulse.

Yet another embodiment of the present invention relates to a signal processing method. The method comprises: acquiring a sample data series of a signal indicating a touch state quantity detected in a touch panel; determining a frequency spectral distribution by transforming the sample data series into a frequency domain; and detecting a peak in a frequency band of a pulse in the frequency spectral distribution, and finding a frequency of the detected peak so as to determine the pulse.

Optional combinations of the aforementioned constituting elements, and implementations of the invention in the form of methods, apparatuses, systems, computer programs, data structures, and recording mediums may also be practiced as additional modes of the present invention.

BRIEF DESCRIPTION OF THE DRAWINGS

Embodiments will now be described by way of examples only, with reference to the accompanying drawings which are meant to be exemplary, not limiting, and wherein like elements are numbered alike in several Figures in which.

DETAILED DESCRIPTION OF THE INVENTION

The invention will now be described by reference to the preferred embodiments. This does not intend to limit the scope of the present invention, but to exemplify the invention.

Figure 1:
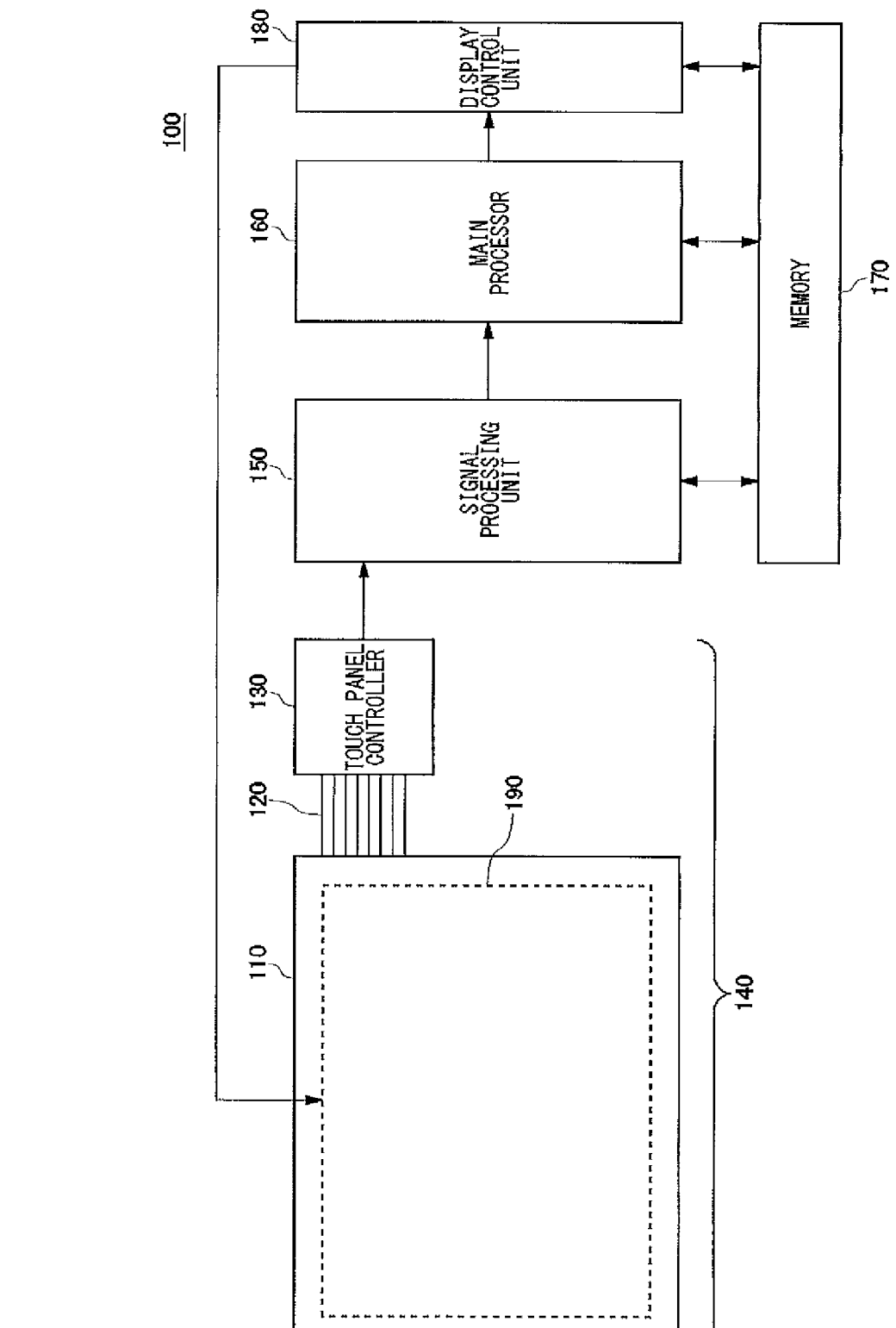
FIG. 1 is a configuration diagram of an information processor according to an embodiment.

FIG. 1 is a configuration diagram of an information processor 100 according to an embodiment. Part of or all of the functional configurations in the information processor 100 shown in FIG. 1 may be implemented by hardware, software, or a combination thereof provided in a personal computer, a game device, a mobile device, or a mobile terminal, for example.

The information processor 100 comprises a touch panel unit 140, a signal processing unit 150, a main processor 160, a memory 170, a display control unit 180, and a display 190.

The touch panel 140 includes a touch panel 110 and a touch panel controller 130 connected to the touch panel 110 by a flexible substrate 120.

The touch panel 110 is an input device capable of sensing, using various methods, a point (position) of contact (hereinafter, "touch point (position)") by a finger or the like and parameters such as electrostatic capacitance or electric resistance indicating the contact state at the touch point (position) (hereinafter, referred to as "touch state quantity"). The touch panel 110 is mounted on the display 190, which may be a liquid crystal display or an organic EL (electroluminescence) display, for example. This allows a user viewing the screen of the display 190 to provide an input for control on the screen by directly touching the touch panel 110 with a finger.

The touch panel 110 is a capacitive type touch panel, for example. The touch panel controller 130 measures an amount of variation in electrostatic capacitance at respective points on the touch panel 110 so as to detect a position of a touch point and an electrostatic capacitance value at the touch point. When a human finger touches the touch panel 110, the pulsation causes the electrostatic capacitance to vary. This is because very small movement of the finger coordinated with the pulsation and variation in the bloodstream affect the electrostatic capacitance of the touch point. This can be taken advantage of to measure the pulse of the user touching the touch panel 110.

In order to measure the pulse according to the embodiment, the touch panel unit 140 should meet the following conditions.

(1) The unit is capable of scanning touch points at a sampling frequency of 20 Hz or more.

Since the pulse of a human being is generally accommodated with a range of 50-200 [pulses/minute], the frequency of the pulse signal would be 0.5 Hz-2 Hz. Generally, the sampling frequency required for measurement is twice or larger than the frequency of the target of measurement. For high-precision measurement, the sampling frequency of 5-10 times the frequency of the target is necessary. Therefore, assuming the sampling frequency of 10 times that of the target, the maximum sampling frequency necessary will be 2×10=20 Hz. This value is implemented in an ordinary capacitive touch panel relatively easily and is not particularly an excessive requirement for performance.

(2) Time series variation (amplitude) in electrostatic capacitance for each touch point can be acquired.

Time series variation in electrostatic capacitance is time series variation in the difference between an electrostatic measurement occurring when the touch panel is touched and an electrostatic measurement occurring when the touch panel is not touched.

(3) Preferably, the adaptive gain control can be temporarily suspended.

Some capacitive touch panels are designed to adopt adaptive gain control or automatic gain control for adjusting the touch sensitivity adaptively and automatically so as to maintain the output constant by adjusting the sensitivity. This is useful to implement touch panel sensing that is stable in the event of variation in environmental noise. Conversely, variation in the touch sensitivity results in the signal amplitude becoming discontinuous before and after a change in the sensitivity, producing unstable measurements of time series variation of electrostatic capacitance for the purpose of measuring the pulse. It is therefore preferable to fix the touch sensitivity while the pulse is being measured. It should be reminded that adaptive gain control will not be a problem in applications that permit occasional unstable measurements resulting from a change in touch sensitivity. Sensitivity adjustment that is not so frequent may not require suspension of adaptive gain control.

The description above assumes the touch panel 110 of capacitive type. The touch panel need not necessarily be of capacitive type. Touch panels of any type capable of acquiring measurements of some quantity in the form of time series data according to the pulse of a finger can be used. For example, a high-sensitivity pressure-sensitive touch panel with high pressure resolution can be used. An optical touch panel can also be used capable of high-resolution acquisition of the intensity of near infrared reflection or absorption by hemoglobin including in the bloodstream of the finger. The touch panel 110 may be of any type not given as examples above so long as it is capable of sensing the touch state quantity that varies according to the pulsation in the form of some physical quantity.

The signal processing unit 150 acquires time series data for electrostatic capacitance at the touch point detected by the touch panel controller 130 and determines the pulse of the touching user by subjecting the data to signal processing, reading and writing data in the memory 170.

The main processor 160 uses the pulse data determined by the signal processing unit 150 and runs an application such as a game. For example, the main processor 160 adjusts a game parameter in accordance with the value of the measured pulse, displays an index related to the pulse while the game is being run, or notifies the user of the index.

The display control unit 180 displays a game screen or an output screen for an application on the display 190. The display control unit 180 also displays, on the display 190, a guide for guiding the user to a position on the touch panel 110 that should be touched by the user, or displays, on the display 190, a guide for guiding the user to continue to touch the touch panel 110 until a time necessary for measurement of pulse elapses.

Figure 2:
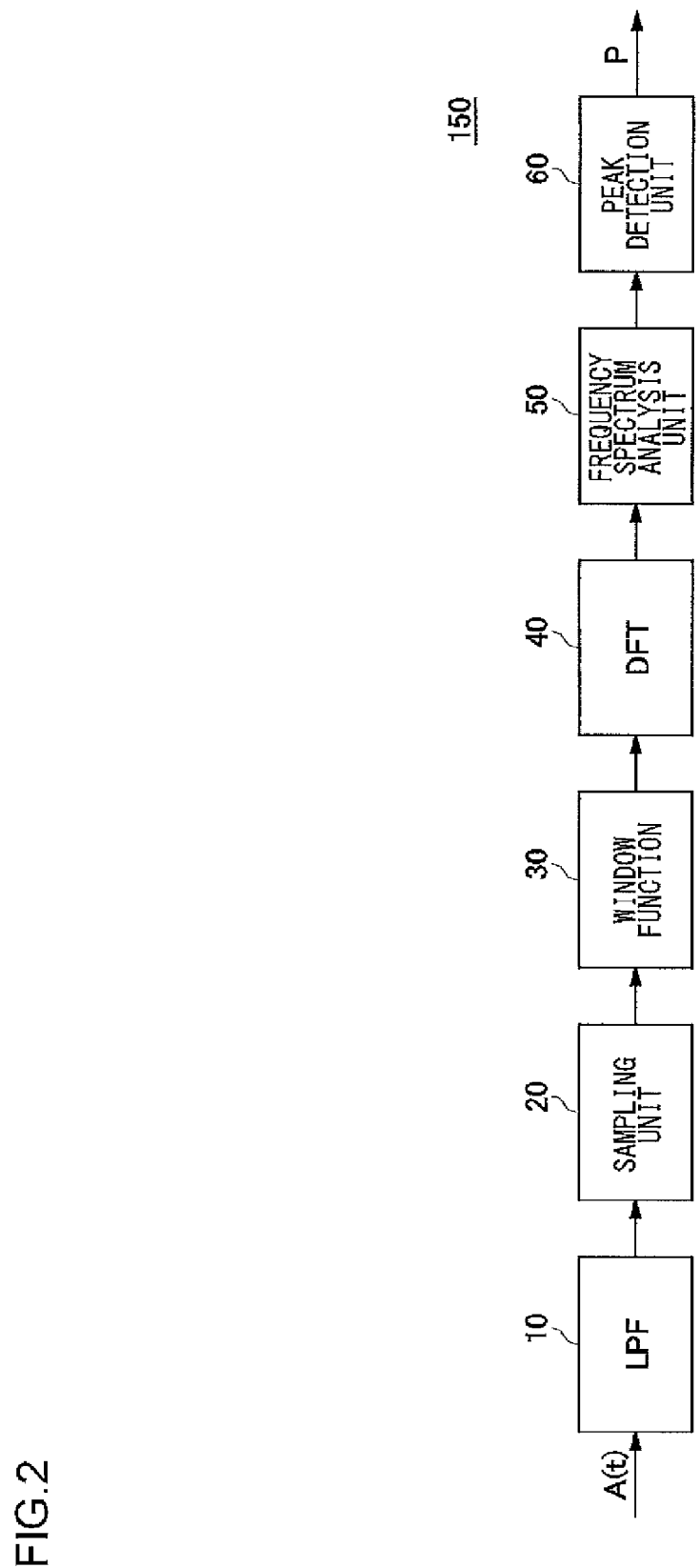
FIG. 2 shows functional features of the signal processing unit of FIG. 1.

FIG. 2 shows functional features of the signal processing unit 150. The signal processing unit 150 includes a low-pass filter (LPF) 10, a sampling unit 20, a window function processing unit 30, a discrete Fourier transform (DFT) unit 40, a frequency spectrum analysis unit 50, and a peak detection unit 60.

The touch panel controller 130 outputs, as touch point data, coordinates (X, Y) of n touch points and the amplitude A of electrostatic capacitance, along with a time T of measurement. The signal processing unit 150 acquires the following time series data. In the case of a multitouch panel capable of sensing multiple touch points at a time, n≥2. In the case of a touch panel only capable of sensing a single point, n=1.

$$T=t0, (X1,Y1,A1), (X2,Y2,A2), \ldots, (Xn,Yn,An)$$

$$T=t1, (X1,Y1,A1), (X2,Y2,A2), \ldots, (Xn,Yn,An)$$

$$T=t2, (X1,Y1,A1), (X2,Y2,A2), \ldots, (Xn,Yn,An) \ldots$$

To highlight the first touch point, the time series data for the amplitude of electrostatic capacitance is obtained as time series discrete sampling data A1(*t*)={A1(*t*0), A1(*t*1), A1(*t*2), . . . }. The sampling rate f2 is obtained as fs=1/(t1−t0)=1/(t2−t1)= . . . . Generally, the time of measurement includes a jitter so that an average value between individual time differences may be used to compute the sampling rate.

The aforementioned time series data for the amplitude of electrostatic capacitance includes information other than the pulse of the human being. For example, the data includes power supply noise and environmental noise. In particular, a touch panel is generally designed with a sampling rate of 30 Hz or more for the purpose of defining a high resolution of time series variation in touch point coordinates. In other words, the data will include frequency components higher than the frequency band 0.5-2 Hz of the pulse.

Thus, the low pass filter 10 filters the amplitude signal A(t) of electrostatic capacitance by a low pass filter for removing frequencies other than that of the pulse and, in particular, removing high frequencies. A 10-tap low pass filter is used and the cut-off frequency fc is defined such that fc=4 Hz, in consideration of the frequency band of the pulse. The characteristic of the low pass filter is preferably tuned in consideration of the frequency characteristic obtained from the touch panel 110 and the noise environment.

For the purpose of frequency spectral analysis, the sampling unit 20 then retrieves a sample data series from the data series for the electrostatic capacitance signal subjected to low pass filtering. The number of samples is preferably a power of 2 so that the samples can be subject to discrete Fourier transform computation later. It will be assumed that 512 samples are retrieved. The larger the number of samples, the higher the precision and the larger the volume of computation. 512-1024 samples will be suitable. Given that the touch panel 110 samples the signal at a rate of 60 samples a second, a data acquisition period of about 8 seconds should be provided to retrieve 512 samples.

The window function processing unit 30 applies a window function to the sample data series for precise frequency analysis. It will be assumed here that precision of the frequency spectrum is given high weight so that a Hamming window is used. Other window functions may be used to adapt to the characteristic of the output data from the touch panel 110.

The discrete Fourier transform unit 40 applies discrete Fourier transform (DFT) to the sample data series processed by the window function, transforming the sample data into the frequency domain data. The frequency spectrum analysis unit 50 determines a frequency spectral distribution based on the sample data transformed into the frequency domain data.

The peak detection unit 60 detects a peak corresponding to the pulse in the spectral distribution obtained by the frequency spectral analysis unit 50. If a peak in the frequency band corresponding to 0.5 Hz-2 Hz is larger than the other peaks and is a clear monomodal peak, the peak should be identified as the pulse. The peak detection unit 60 finds the frequency of the peak so as to determine the pulse P [pulses/minute].

Figure 3:
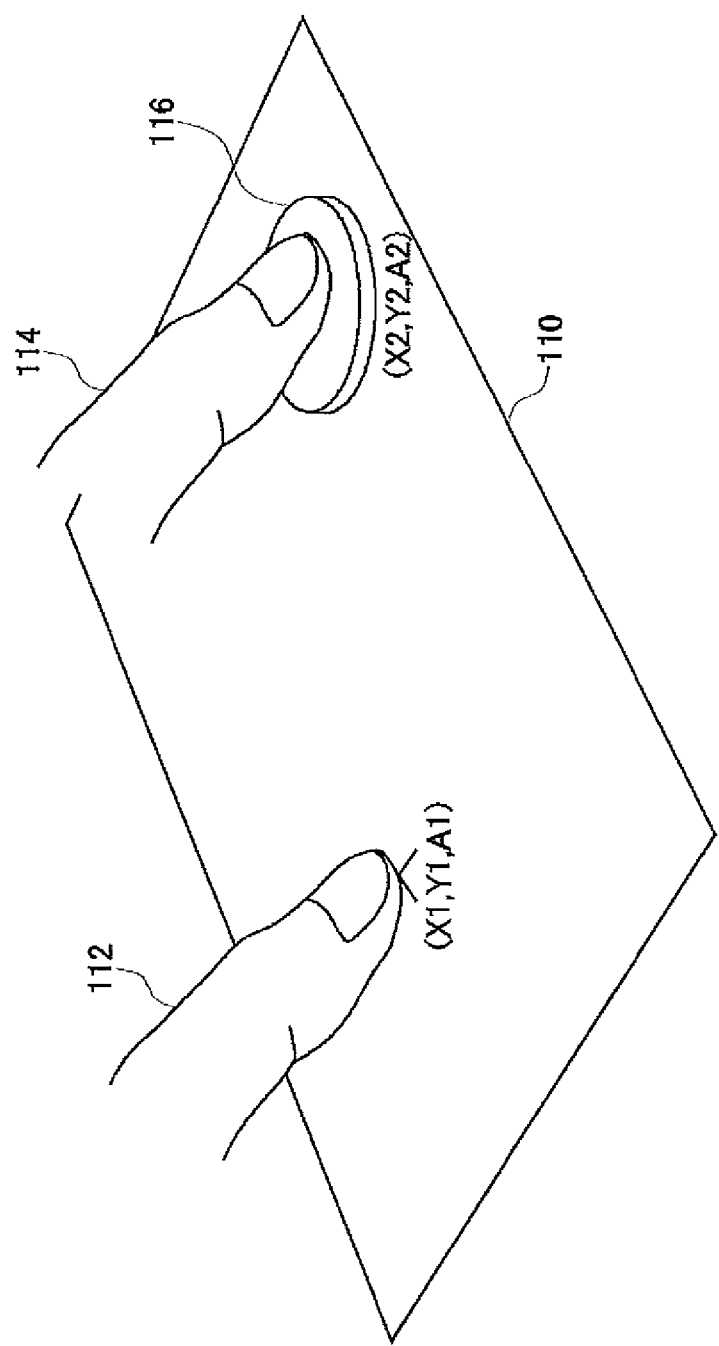
FIG. 3 shows how the finger touches the touch panel.

FIG. 3 shows how the finger touches the touch panel 110. When a finger 112 directly touches a certain position (X1, Y1) on the touch panel 110, an electrostatic capacitance amplitude signal A1 is detected. When a finger 114 touches another position (X2, Y2) on the touch panel 110 via a coin 116, an electrostatic capacitance amplitude signal A2 is detected.

Figure 4:
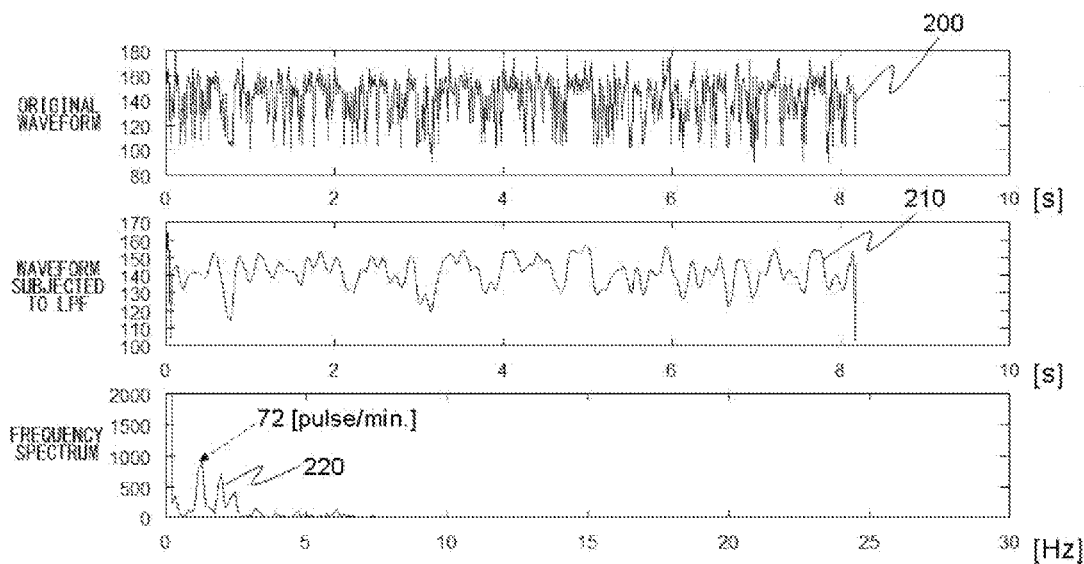
FIG. 4 illustrates signal processing on the electrostatic capacitance amplitude signal detected when a certain position on the touch panel is directly touched by the finger.

FIG. 4 illustrates signal processing on the electrostatic capacitance amplitude signal A1 detected when the position (X1, Y1) on the touch panel 110 is directly touched by the finger 112 as shown in FIG. 3.

The top graph of FIG. 4 shows an original waveform 200 of the electrostatic capacitance amplitude signal A1. The horizontal axis represents time (in units of seconds). The middle graph of FIG. 4 shows a signal 210 produced by filtering the original waveform 200 of the electrostatic capacitance signal A1 by using a low pass filter so as to remove high-frequency components. The bottom graph of FIG. 4 shows a frequency spectrum 220 produced by transforming the signal 210 subjected to low pass filtering into the frequency domain signal. The horizontal axis represents frequency (in units of Hz). In the frequency band 0.5 Hz-2 Hz of the pulse, one peak is found. The frequency of the peak is converted into the pulse of 72 pulses/minute.

Thus, when the touch panel 110 is directly touched by the finger 112, the electrostatic capacitance signal detected at the touch point includes frequency components corresponding to the pulse. By removing high-frequency components from the electrostatic capacitance signal and subjecting the signal to frequency spectral analysis, the frequency spectrum corresponding to the pulse can be identified. The frequency spectral distribution includes multiple peaks. However, because it is known that the frequency band of the human pulse is accommodated within the range of 5-2 Hz, the frequency spectrum of the pulse can be isolated. Even if a spectrum induced by another factor (e.g. noise) is mixed in the frequency band of the pulse, the frequency spectrum of the pulse can be isolated if the frequency spectrum of the pulse is sufficiently larger.

Figure 5:
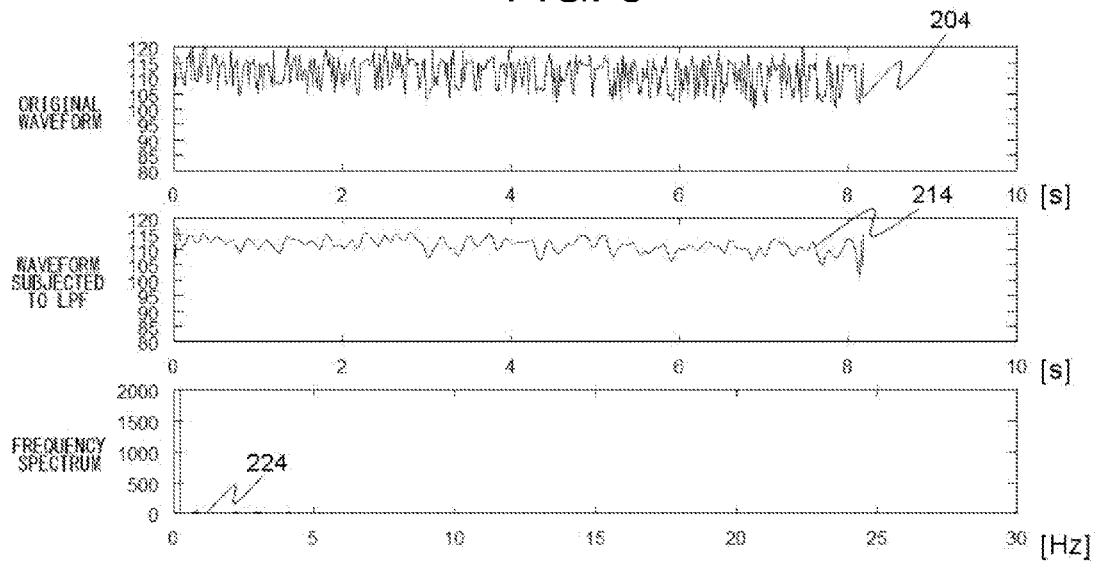
FIG. 5 illustrates signal processing on the electrostatic capacitance amplitude signal A detected when another position on the touch panel is indirectly touched by the finger.

FIG. 5 illustrates signal processing on the electrostatic capacitance amplitude signal A2 detected when the other position (X2, Y2) on the touch panel 110 is indirectly touched by the finger 114 as shown in FIG. 3.

The top graph of FIG. 5 shows an original waveform 204 of the electrostatic capacitance amplitude signal A2. The middle graph of FIG. 5 shows a signal 214 produced by filtering the original waveform 204 of the electrostatic capacitance signal A2 by using a low pass filter so as to remove high-frequency components. The bottom graph of FIG. 5 shows a frequency spectrum 224 produced by transforming the signal 214 subjected to low pass filtering into the frequency domain signal. No sharp peaks are observed in the frequency spectrum 224, including the frequency band 0.5-2 Hz of the pulse. By sandwiching the coin 116 between the touch panel 110 and the finger 114, the pulse does not induce a change in the electrostatic capacitance and so is not detected. A similar situation results when the touch panel 110 is touched by a stylus compatible with touch panels of capacitive type. Therefore, distinction can be made as to whether the touch panel 110 is being touched by a human finger or by something else.

There is a need to make distinction as to whether the touch panel 110 is touched by a human finger or something else, or whether the user is wearing anything on his/her finger, for the purpose authentication etc. In such a case, whether the touch panel is being touched by a human finger can be determined by detecting whether a pulse is detected in the signal waveform detected from the touch panel 110.

Figure 6:
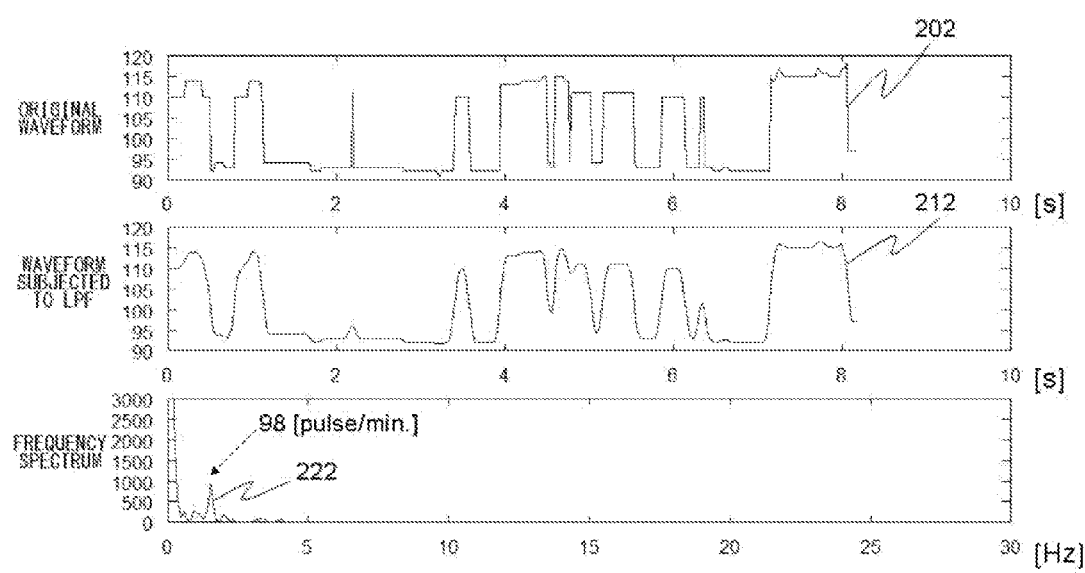
FIG. 6 illustrates signal processing on the electrostatic capacitance amplitude signal detected when a touch panel of an alternative specification is touched by the finger.

FIG. 6 illustrates signal processing on the electrostatic capacitance amplitude signal detected when a capacitive touch panel of an alternative specification is touched by the finger. Different touch panels may employ different methods for signal acquisition and signal processing even if all of them are of capacitive type. Conditions such as S/N ratio of a detection signal may also differ, resulting in different signal waveforms.

The top graph of FIG. 6 shows an original waveform 202 of the electrostatic capacitance amplitude signal. The middle graph of FIG. 6 shows a signal 212 produced by filtering the original waveform 202 of the electrostatic capacitance signal A1 by using a low pass filter so as to remove high-frequency components. The bottom graph of FIG. 6 shows a frequency spectrum 222 produced by transforming the signal 212 subjected to low pass filtering into the frequency domain signal. In the frequency band 0.5 Hz-2 Hz of the pulse, one peak is found. The frequency of the peak is converted into the pulse of 98 pulses/minute. Thus, difference in the types of touch panels may result in large difference in the waveform of the electrostatic capacitance signal detected. Nevertheless, peaks corresponding to pulses show up in the frequency spectral distribution unmistakably so that the pulse can be measured.

As described above, the use of the touch panel unit 140 enables measurement of the user's pulse while the user is touching the touch panel 110 with a finger. A description will now be given of the user interface for guiding the user to touch the touch panel 110 to measure the pulse, and applications that use the user's pulse thus measured.

Figure 7A:
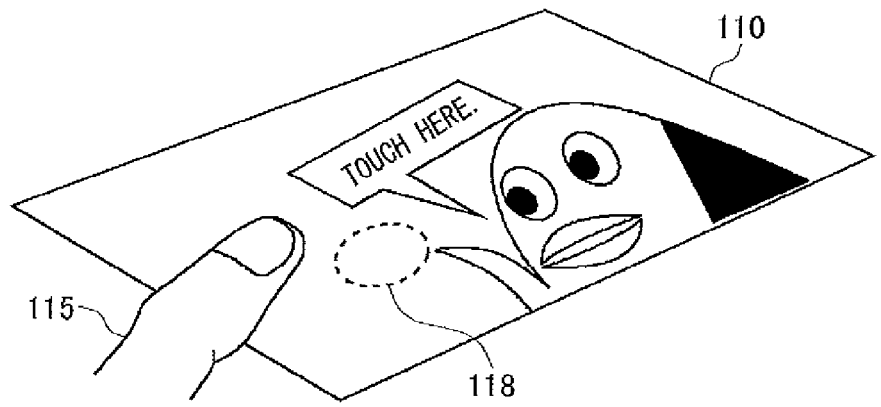
FIGS. 7A-7C illustrate display screens that guide the user to touch the touch panel.
Figure 7B:
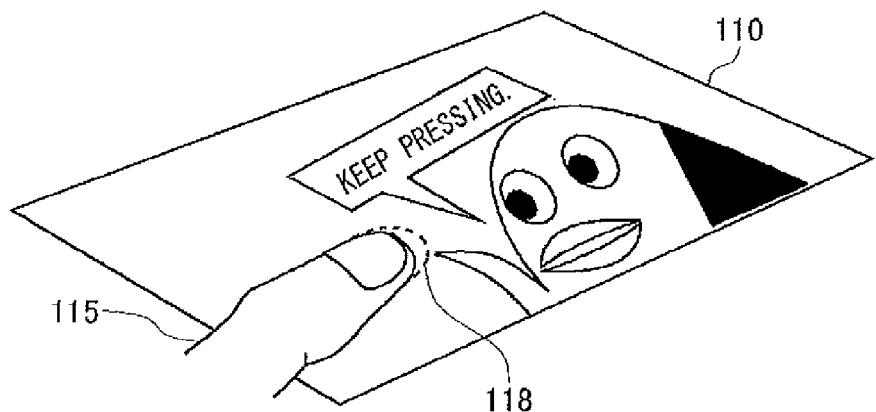
Figure 7C:
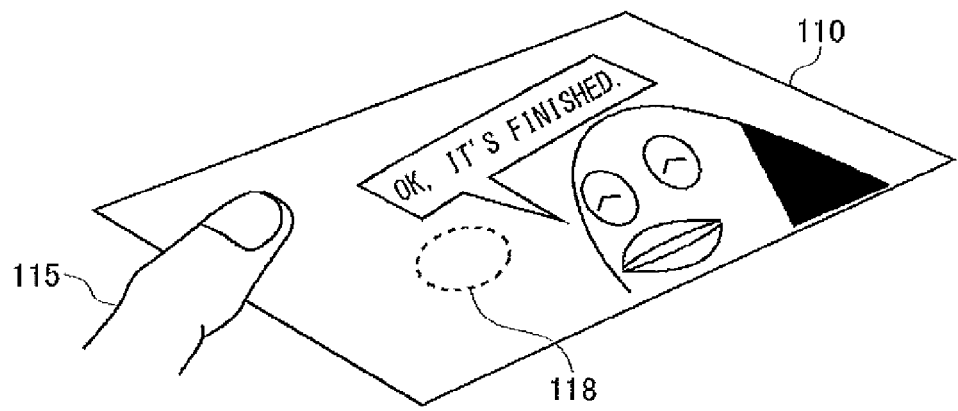

FIGS. 7A-7C illustrate display screens that guide the user to touch the touch panel 110. In order to measure the user's pulse, it is necessary to cause the user to touch the touch panel 110 for a duration of time necessary to acquire the number of samples required for measurement.

As shown in FIG. 7A, a character on the touch panel 110 (strictly speaking, on the screen of the display 190 located below the touch panel 110) points to an area 118 bounded by a dotted line, saying "Touch here!" so as to guide the user to touch the area.

As the guided user touches the area 118 with a finger 115 as shown in FIG. 7B, the character says "Keep pressing!", prompting the user to continue to touch the area 118. When a predetermined period of time for measurement (e.g. 5-8 seconds) elapses, the character changes the facial expression and says "OK, it is finished!!" as shown in FIG. 7C, and the user removes the finger 115 from the touch panel 110.

While the user's finger 115 remains touching the touch panel 110, the signal processing unit 150 subjects the value of electrostatic capacitance amplitude for the touch point obtained from the touch panel 140 to spectral analysis so as to measure the user's pulse. In this way, the user can have his or her pulse measured without being aware of the process.

The pulse can be measured at any position on the touch panel 110. For more precise sensing, however, the location of touch by the finger may be restricted. In this case, the area 118 of FIGS. 7A-7C bounded by the dotted line may be displayed at a position where high-precision sensing is possible so that the user is guided to the position that should be touched by the finger.

In the examples of FIGS. 7A-7C, the character displayed on the screen prompts the user to press the touch panel 110 for a certain duration of time. The user may be informed that the pulse is being measured with a flash of an indicator.

Figure 8:
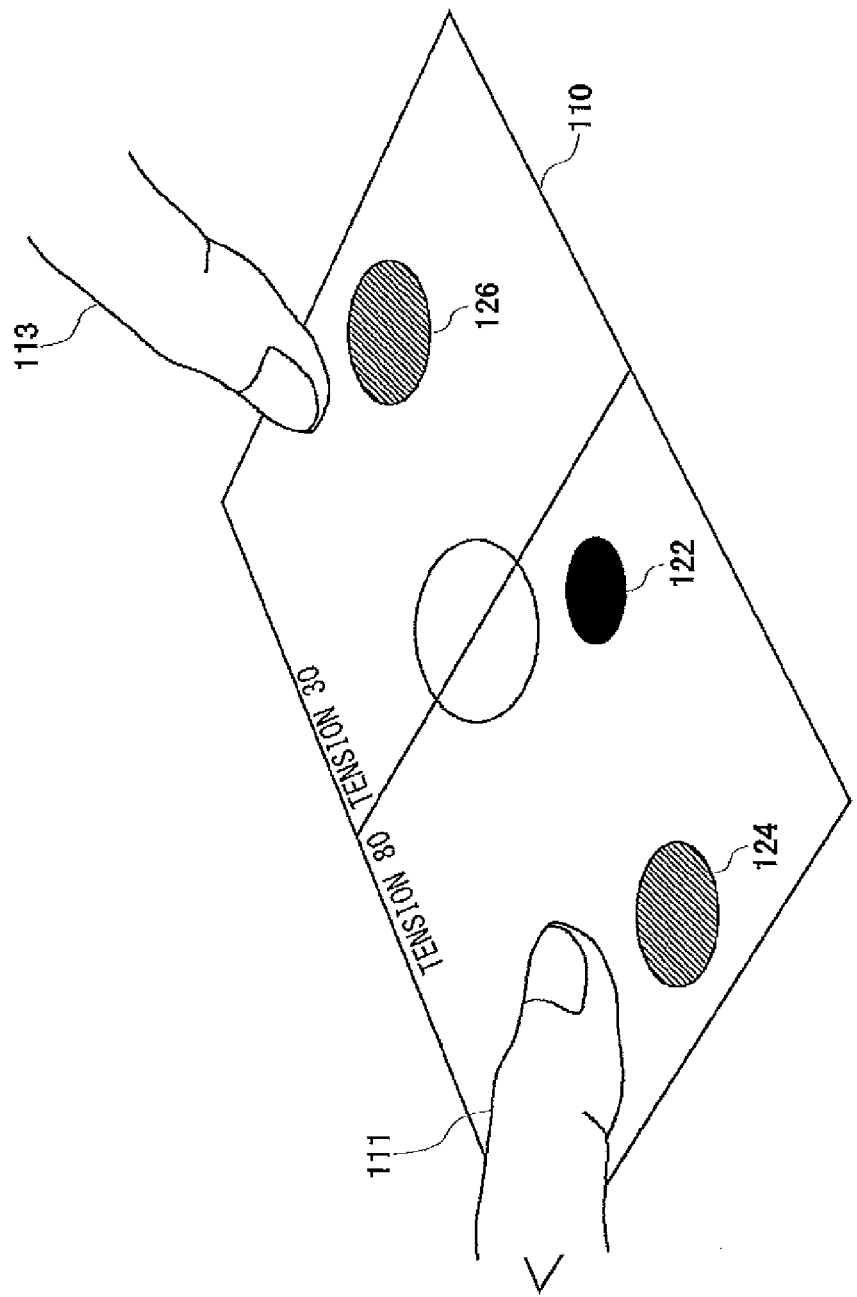
FIG. 8 shows an example where the user's pulse is measured on a game screen.

FIG. 8 shows an example where the user's pulse is measured on a game screen. An air hockey game is displayed on the display screen of the touch panel 110. The first user controls his or her mallet 124 with a finger 111 to hit a disc 122. The second user controls his or her mallet 126 with a filter 113 to hit the disc 122.

The first and second users touch the touch panel 110 with the fingers 111 and 113 while controlling the mallets 124 and 126, respectively. The touch point is moved, but the fingers 111 and 113 continue to touch the touch panel 110 for a certain period of time. Therefore, time series data including touch position coordinates and electrostatic capacitance amplitude is obtained as follows for the first user, if the touch panel 110 is compatible with multitouch operation.

$$T=t1,(X1,Y1,A1)$$

$$T=t2,(X2,Y2,A2)$$

$$T=t3,(X3,Y3,A3)$$

$$\ldots$$

$$T=tn,(Xn,Yn,An)$$

Time series data $A1=\{A1(t1), A2(t2), A3(t3), \ldots, An(tn)\}$ for electrostatic capacitance amplitude for the first user is obtained at varying touch positions. Similarly, time series data $B1=\{B1(t1), B2(t2), B3(t3), \ldots, Bn(tn)\}$ for electrostatic capacitance amplitude for the second user is obtained at varying touch positions.

The touch panel unit 140 compatible with multitouch operation outputs the time series data A1 for electrostatic capacitance amplitude for the first user and the time series data B1 for electrostatic capacitance amplitude for the second user at the same time. The signal processing unit 150 can distinguish between them according to the difference in touch position. The first and second users of the air hockey game touch the touch panel 110 in their own courts shown on the display screen and do not touch the touch panel 110 in the opponent's court. Therefore, the electrostatic capacitance amplitude signal for the first user and the electrostatic capacitance amplitude signal for the second user can be distinguished by determining which court the touch position coordinates (X, Y) belong.

Measurements of the pulses of the first and second users may be used in the game application to display the users' tension as shown in FIG. 8. In this example, the pulse of the first user is increased with the advancement of the game so that a high value "tension 80" is displayed in the first user's court. Meanwhile, the pulse of the second user is not increased so that a low value "tension 30" is displayed in the second user's court.

The parameter of the game application may be changed depending on the measured pulse. For example, the value of a parameter indicating excitation of a game character may be increased with an increase of the pulse. Alternatively or additionally, the value of a parameter related to the offensive power or physical power of the game character may be decreased with an increase of the pulse. Alternatively or additionally, when the user's pulse is increased, the value indicating the character's tension may be increased and the character in the game may be shown stressed. In the case of a racing game, the speed of the vehicle may be varied depending on the pulse. Time-dependent variation in the pulse may be reflected in the development of the game. Further, as the pulse is increased, the speed of advancement of the game may be increased, the tempo of the music used in the game may be increased, or the number may be changed.

Thus, the result of measuring the pulse can be used in the presentation of a game application. In this case, the precision of measurements of the pulse is not of serious concern.

In the example described above, there is no need to cause the user to touch the touch panel 110 knowingly in order to measure the pulse. The pulse is measured and used in the game in a manner unknown to the user, while the user is playing the game by touching the touch panel 110. Therefore, the user is not stressed at all. Further, with the touch panel 110 compatible with multitouch operation, the pulse of multiple users can be measured and used in a multiuser game.

A single user may use multiple fingers in a multitouch operation on the touch panel 110, or multiple users may perform a multitouch operation. Distinction between these is also possible. If the sampling unit 20 acquires multiple time series data for electrostatic capacitance amplitude in response to a multitouch operation as described above, and if the multitouch operation is by multiple users, the peak detection unit 60 generally detects multiple peaks in the frequency band of the pulse, obtaining multiple different pulse values. In contrast, if the multitouch operation is by a single user, only one peak should be detected in the frequency band of the pulse and only one pulse value should be obtained. Generally, the pulse value differs from one user to another. Therefore, if a multitouch operation is detected, and if substantially the same pulse values are detected, the main processor 160 can assume that a single user performed a multitouch operation except in cases where the pulse values of multiple users happen to match. Conversely, if different pulse values are detected concurrently, it can be assumed that multiple users performed a multitouch operation.

Figure 9:
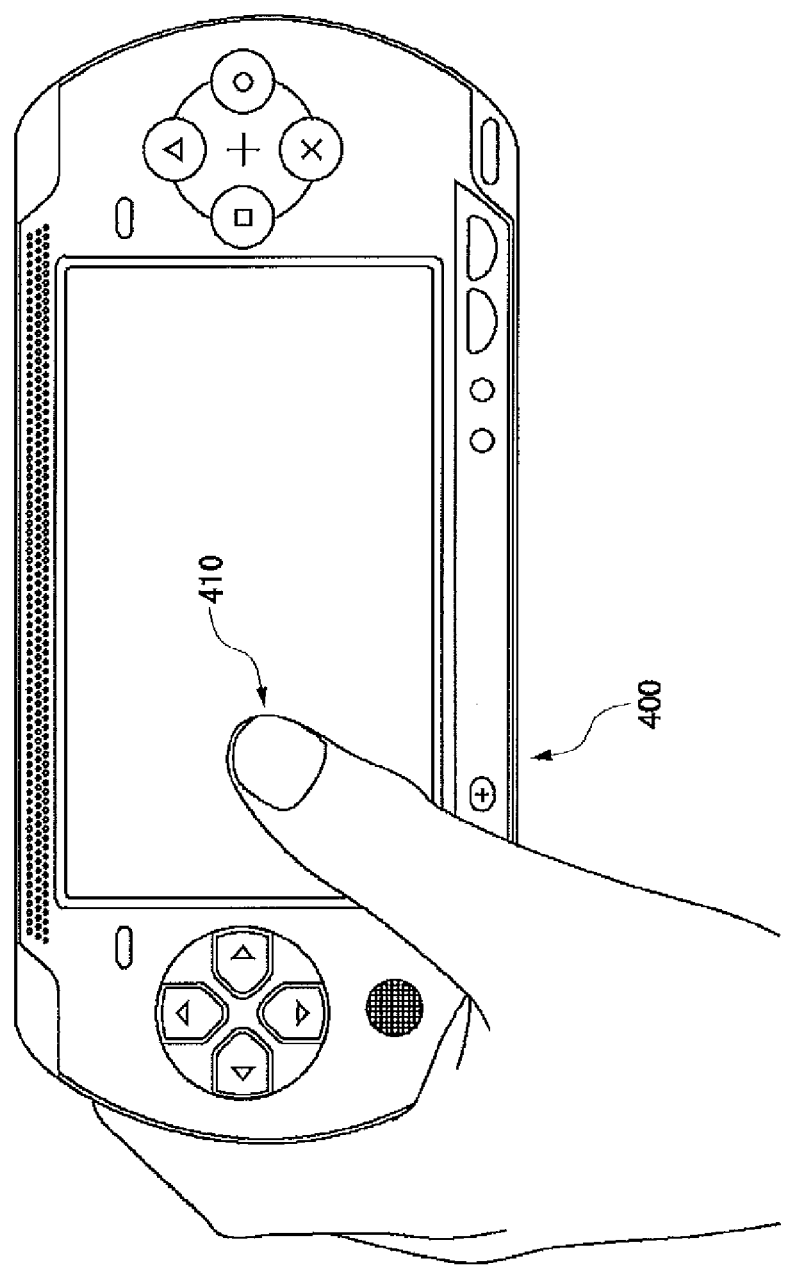
FIG. 9 illustrates a method of measuring the user's pulse in a mobile game device.

FIG. 9 illustrates a method of measuring the user's pulse in a mobile game device 400. As the user grips the mobile game device 400, the thumb of the user touches the liquid crystal display of the mobile game device 400. The user's pulse may be measured in accordance with variation in the electrostatic capacitance detected by the touch panel unit in this location of grip 410.

In the case of the mobile game device 400 with a touch pad or a touch panel provided with a touch sensor on both the front and rear surfaces, a finger other than the thumb must be touching the touch sensor on the rear surface so that the pulse may be detected by the touch sensor on the rear surface. According to this method, the finger remains touching the touch sensor on the rear surface even while the thumb is not touching the front touch panel so long as the user is gripping the mobile game device 400. Therefore, more stable and continuous measurement of the pulse is possible.

As described above, according to the information processor of the embodiment, the user's pulse can be measured easily by using a touch panel, and the pulse can be used as an input to an application or fed back to the user. This improves the functionality of the device as a human interface device. By allowing an input of the pulse as biological information, interaction between the user and the application is facilitated, feasibility of applications related to exercise or health management is improved, and sense of presence is provided to applications like games.

Described above is an explanation based on an exemplary embodiment. The embodiment is intended to be illustrative only and it will be obvious to those skilled in the art that various modifications to constituting elements and processes could be developed and that such modifications are also within the scope of the present invention.

In the above description, the signal processing unit 150 acquires a signal indicating a touch state quantity output from the touch panel controller 130 and subjects the signal to signal processing so as to determine the pulse by frequency spectral analysis. The functionality of the signal processing unit 150 may be implemented inside the touch panel controller 130 as a dedicated circuit or a dedicated program. The pulse occurs only once per a second or so. Therefore, signal processing need not meet severe real time requirements. The circuit or the program need only perform one operation per a second. Therefore, the processing capability of the touch panel controller 130 connected to the touch panel 110 via the flexible substrate 120 is sufficient to address the need.

The invention claimed is:

1. A signal processing device comprising:
a sampling unit configured to acquire a sample data series of a signal indicating a touch state quantity detected in a touch panel, the touch state quantity including an electrostatic capacitance value at a touch point;
an analysis unit configured to determine a frequency spectral distribution by transforming the sample data series into a frequency domain; and
a peak detection unit configured to detect a peak in a frequency band of a pulse in the frequency spectral distribution, and to find a frequency of the detected peak so as to determine the pulse; wherein
acquisition of the touch state quantity occurs during temporary suspension of gain control used to adjust touch sensitivity of the touch panel when detecting a position of the touch point.

2. A touch panel unit comprising:
a touch panel; and
a touch panel controller configured to detect a position of a touch point on the touch panel and a touch state quantity, the touch state quantity including an electrostatic capacitance value at the touch point, and to output the position and the quantity as a signal,
wherein the touch panel controller includes:
a sampling unit configured to acquire a sample data series of a signal indicating the touch state quantity;
an analysis unit configured to determine a frequency spectral distribution by transforming the sample data series into a frequency domain; and
a peak detection unit configured to detect a peak in a frequency band of a pulse in a frequency spectral distribution, and to find a frequency of the detected peak so as to determine the pulse; wherein
acquisition of the touch state quantity occurs during temporary suspension of gain control used to adjust touch sensitivity of the touch panel when detecting a position of the touch point.

3. An information processing device comprising:
a touch panel unit including a touch panel and a touch panel controller configured to detect a position of a touch point on the touch panel and a touch state quantity, the touch state quantity including an electrostatic capacitance value at the touch point, and to output the position and the quantity as a signal;
a signal processing unit configured to subject an output signal from the touch panel controller to signal processing;
a main processor configured to run an application; and
a display controller configured to control data that should be displayed on a display device provided in the touch panel,
wherein the signal processing unit includes:
a sampling unit configured to acquire a sample data series of a signal indicating a touch state quantity detected in a touch panel;
an analysis unit configured to determine a frequency spectral distribution by transforming the sample data series into a frequency domain; and
a peak detection unit configured to detect a peak in a frequency band of a pulse in the frequency spectral distribution, and to find a frequency of the detected peak so as to determine the pulse; wherein acquisition of the touch state quantity occurs during temporary suspension of gain control used to adjust touch sensitivity of the touch panel when detecting a position of the touch point.

4. The information processing device according to claim 3, wherein the display controller displays, on a screen of the display device, a guide for guiding a user to a position on the touch panel that should be touched.

5. The information processing device according to claim 3, wherein the display controller displays a guide for guiding a user to continue to touch the touch panel until a necessary period of time elapses for measurement of the pulse.

6. The information processing device according to claim 3, wherein the signal processing unit determines the pulse of the user by subjecting the touch state quantity to frequency spectral analysis, the touch state quantity being detected while the user continues to touch the touch panel during a predetermined period of time in order to provide user input.

7. The information processing device according to claim 3, wherein the main processor adjusts a parameter of a game application in accordance with a value of the pulse measured.

8. The information processing device according to claim 3, wherein, if the peak detection unit does not detect a peak in a frequency band of the pulse, the main processor determines that the touch panel is not touched by a human finger.

9. The information processing device according to claim 3,
wherein the touch panel unit is compatible with a multitouch operation and the sampling unit acquires a plurality of sample data series in response to a multitouch operation;
wherein, if the peak detection unit detects a plurality of peaks in the frequency band of the pulse and obtains a plurality of different pulse values, the main processor determines that the multitouch operation is by a plurality of users, and
wherein, if the peak detection unit detects substantially one peak in the frequency band of the pulse and obtains one pulse value, the main processor determines that the multitouch operation is by a single user.

10. A signal processing method comprising:
acquiring a sample data series of a signal indicating a touch state quantity detected in a touch panel, the touch state quantity including an electrostatic capacitance value at a touch point;
determining a frequency spectral distribution by transforming the sample data series into a frequency domain; and
detecting a peak in a frequency band of a pulse in the frequency spectral distribution, and finding a frequency of the detected peak so as to determine the pulse; wherein
acquiring the touch state quantity occurs during temporary suspension of gain control used to adjust touch sensitivity of the touch panel when detecting a position of the touch point.

11. A non-transitory computer-readable recording medium containing a computer program, which when executed by a computer, causes the computer to carry out actions, comprising:
acquiring a sample data series of a signal indicating a touch state quantity detected in a touch panel, the touch state quantity including an electrostatic capacitance value at a touch point;
determining a frequency spectral distribution by transforming the sample data series into a frequency domain; and
detecting a peak in a frequency band of a pulse in the frequency spectral distribution and to find a frequency of the detected peak so as to determine the pulse;
wherein acquiring the touch state quantity occurs during temporary suspension of gain control used to adjust touch sensitivity of the touch panel when detecting a position of the touch point.

12. A computer comprising a microprocessor and a non-transitory computer-readable recording medium encoded with a computer program, which when executed by the microprocessor, causes the computer to carry out actions, comprising:
acquiring a sample data series of a signal indicating a touch state quantity detected in a touch panel, the touch state quantity including an electrostatic capacitance value at a touch point;
determining a frequency spectral distribution by transforming the sample data series into a frequency domain; and
detecting a peak in a frequency band of a pulse in the frequency spectral distribution and to find a frequency of the detected peak so as to determine the pulse;
wherein acquiring the touch state quantity occurs during temporary suspension of gain control used to adjust touch sensitivity of the touch panel when detecting a position of the touch point.

* * * * *